United States Patent [19]
Elias

[11] Patent Number: 5,310,742
[45] Date of Patent: May 10, 1994

[54] USES FOR THIOUREYLENES

[76] Inventor: Alan N. Elias, 2984 Alpine Way, Laguna Beach, Calif. 92651

[21] Appl. No.: 982,702

[22] Filed: Nov. 30, 1992

[51] Int. Cl.$^5$ .......................................... A61K 31/505
[52] U.S. Cl. ..................................................... 514/274
[58] Field of Search ........................................ 514/274

[56] References Cited

U.S. PATENT DOCUMENTS

| | | | |
|---|---|---|---|
| 4,457,907 | 7/1984 | Porter | 424/7.1 |
| 4,608,341 | 8/1986 | Ambesi-Impiombato | 435/240 |
| 4,609,622 | 9/1986 | Kohn et al. | 435/29 |
| 4,652,441 | 3/1987 | Okada et al. | 424/19 |
| 4,711,782 | 12/1987 | Okada et al. | 424/455 |
| 4,853,227 | 8/1989 | Kurihara-Bergstrom et al. | 514/359 |
| 4,917,893 | 4/1990 | Okada et al. | 424/423 |
| 4,954,298 | 9/1990 | Yamamoto et al. | 264/4.6 |
| 5,010,092 | 3/1991 | Elfarra | 514/359 |
| 5,061,492 | 10/1991 | Okada | 424/423 |
| 5,087,441 | 2/1992 | Elfarra | 514/359 |
| 5,100,669 | 3/1992 | Hyon et al. | 424/426 |

OTHER PUBLICATIONS

Physician's Desk Reference, pp. 1298-1299, 1510-1511, 1992.

"Effects of Methimazole on Human Lymphocyte Proliferation and Natural Killer Cell Activity," by Brahma S. Sharma and Alan N. Elias, Department of Medicine, University of California at Irvine, vol. 18(4): pp. 449-453, (1987).

"The Immunosuppressive Effect of Methimazole on Cell-Mediated Immunity Is Mediated By Its Capacity To Inhibit Peroxidase and To Scavenge Free Oxygen Radicals," by Csaba Balazs, et al., vol. 25: pp. 7-15, (1986).

"Anti-Thyroid Drugs and Lymphocyte Function, II, The In Vivo Effect of Blastogenesis and Suppressor Cell Activity In Graves' Disease", by Nily Goldrath, et al., Clin. Exp. Immunol. vol. 50: 62-69 (1982).

"Methimazole and Generation of Oxygen Radicals By Monocytes: Potential Role In Immunosuppression," by A. P. Weetman et al., British Medical Journal, vol. 28, Feb. 18, 1984, pp. 518-519.

"Inhibition of The Receptor For Interleukin-2 Induced By Carbimazole: Relevance For The Therapy of Autoimmune Thyroid Disease," by A. Signore, et al., Clin. Exp. Immunol. (1985) 60, pp. 111-116.

"The Effect of Antithyroid Drugs On B and T Cell Activity In Vitro," by R. Wilson, et al., Clinical Endocrinology (1988) 28, pp. 389-397.

"Inhibition of Immunoglobulin-Secreting Cells By Antithyroid Drugs," by Weiss and Davies, Journal of Clinical Endocrinology and Metabolism, vol. 53, No. 6, pp. 1223-1228, 1981.

"Peripheral Blood and Intrathyroidal Mononuclear Cell Populations in Patients With Autoimmune Thyroid Disorders Enumerated Using Monoclonal Antibodies," by J. R. Wall, et al., Journal of Clinical Endocrinology and Metabolism, vol. 56, pp. 164-169, 1982.

Primary Examiner—Frederick E. Waddell
Assistant Examiner—Gregory Hook
Attorney, Agent, or Firm—Knobbe, Martens, Olson & Bear

[57] ABSTRACT

This invention provides new uses for the drugs of the thioureylene class and thiabendazole. These new uses include methods of treatment for a variety of conditions and diseases, including psoriasis, other atopic dermatoses and inflammatory conditions having an autoimmune basis, as well as other autoimmune diseases, including rheumatic disease, and transplant rejection.

7 Claims, 15 Drawing Sheets

USES FOR THIOUREYLENES

This invention relates to new uses for thioureylenes and thiabendazole. More specifically, the invention provides methods of using thioureylenes and thiabendazole for the treatment of psoriasis, rheumatic disease, autoimmune disease, and transplant rejection.

BACKGROUND OF THE INVENTION

Psoriasis is a relatively common skin disorder with an incidence that ranges from 0.5% to 3% in different populations. The lowest incidence is seen in North American Indians, and the highest in caucasians of Scandinavian countries. The disease is distinct from other dermatoses associated with epidermal hyperplasia such as ichthyosis, in that inflammatory cell accumulation is a prominent histological feature of psoriasis. The cause of psoriasis is unknown but the disease has a strong genetic component with approximately one-third of patients having affected relatives.

Multiple humoral and immune factors have been implicated in the development of psoriasis. Several of these factors are leucotrienes (IL2, IL3, IL6), some are growth factors TGF-$\alpha$) and some are other cytokines ($\gamma$-interferon). Additionally, increased keratinocyte proliferation, perivascular inflammation of the dermis, neutrophil migration into the epidermis, and increased production of cytokines such as interleukins IL-1 and IL-8 are commonly seen in psoriatic lesions. The lesions exhibit increased expression of molecules such as intercellular adhesion molecule-1 (ICAM-1), endothelial leucocyte adhesion molecule-1 (ELAM-1), and vascular cell adhesion molecule-1 (VCAM-1), which influence lymphocyte and neutrophil migration and retention in the affected skin.

Current hypotheses of the pathogenesis of psoriasis propose that T cell recruitment to the skin endothelium is an initiating event in the development of psoriasis. Release of interferon gamma (IFN-$\gamma$) and tumor necrosis factor-$\alpha$ (TNF-$\alpha$) by activated T cells and macrophages leads to enhanced expression of cellular adhesion molecules on the endothelium (ICAM-1) permitting retention of such activated T cells in the region of the dermal capillaries. Continued production of IFN-$\gamma$, as well as other leucotrienes such as IL-6 and IL-8 transforms normal keratinocytes (KC) to express an increased number of receptors for ICAM-1, and produce enhanced amounts of transforming growth factor-$\alpha$ (TGF-$\alpha$). Continued production of TGF-$\alpha$ by keratinocytes is associated with decreased negative feedback effects of IFN-$\gamma$ on TGF-$\alpha$ production which is linked to markedly decreased expression of type II histocompatibility antigen (HLA-DR) on the keratinocytes. This in turn is associated with less growth inhibition and development of the psoriatic plaque.

Methotrexate, etretinate, and more recently cyclosporine have been used in the treatment of psoriasis. All these agents have significant side effects and some are only effective in specific forms of psoriasis. Etretinate, for example, is most effective in erythrodermic and pustular psoriasis but is not effective in chronic plaque psoriasis. Its use is further restricted to males and females beyond their reproductive years. The use of the immunosuppressive agents methotrexate and cyclosporine can potentially result in severe toxic reactions.

Autoimmune disease is any of a large group of disorders in which tissue injury is associated with humoral or cell-mediated responses to the body's own constituents. Such disorders may be systemic or organ specific. Rheumatic disease, a type of autoimmune disease, is any of a variety of disorders characterized by inflammation, degeneration, or metabolic derangement of the connective tissue structures of the body. Transplant rejection is an immune reaction seen in patients having received an organ or tissue graft from another individual.

Methotrexate and cyclosporine are also administered in the treatment of rheumatoid arthritis. Another immunosuppressant, azathioprine, is used in the treatment of rheumatoid arthritis and organ transplant rejection. Use of these immunosuppressants results in the risk of severe bone marrow depression and severe toxic reactions.

Accordingly, there is an urgent need for development and identification of relatively non-toxic agents that are effective in the treatment of patients with psoriasis, rheumatoid disease, autoimmune disease, and transplant rejection.

The anti-thyroid thioureylenes, which include propylthiouracil, methimazole, and carbimazole, are often used as first line treatment for patients with hyperthyroidism. Another thioureylene, methylthiouracil, has also been used in the past as an anti-thyroid compound. In developing countries, they are generally the only agents used to treat patients with hyperthyroidism, and have been used continuously for this purpose for decades. The principal effect of these drugs is to impair thyroid hormone biosynthesis and restore thyroid hormone levels to the euthyroid range.

In addition to their effects on thyroid hormone biosynthesis, this class of drugs has been shown to exhibit immune modulatory effects. In in vitro studies using peripheral blood lymphocytes (PBL), propylthiouracil (2,3-dihydro-6-propyl-2-thioxo-4(1H)-pyrimidinone, PTU), and the related thioureylene methimazole (2-mercapto 1-methylimidazole, MMI), were shown to decrease IgM and IgG production and decrease the activity of immunoglobulin-secreting cells in plaque forming assays. MMI is also known to augment natural killer cell (NK) activity. Peripheral blood lymphocytes obtained from patients with Graves' disease, believed to be an autoimmune disorder, when cultured in the presence of PTU and MMI showed a significantly increased percentage of total and suppressor/cytotoxic cells and reduced activated lymphocytes when compared to non-PTU and non-MMI treated PBL. In addition, thioureylenes act as free radical scavengers.

The incidence of side effects from PTU and MMI as currently used is very low. The most serious side effect is agranulocytosis with a maximal incidence of 1 in 500. There is very little difference in the incidence of this side effect between the two thioureylenes. If the drug is discontinued, recovery is the rule.

The most common drug-related side effect is the development of a mild, sometimes purpuric, papular rash. The rash often subsides without interrupting treatment. Other less frequent side effects consist of pain and stiffness in the joints, paresthesia, headaches, nausea, and loss or depigmentation of the hair. Drug fever, hepatitis and nephritis are extremely rare.

Thiabendazole, (2-(4-thiazolyl)-1H-benzimidazole) an anthelmintic used to treat patients with parasitic infections, is closely related in chemical structure to the thioureylenes. The precise mode of action of thiabendazole on parasites is unknown. Common side effects associated with thiabendazole therapy include gastrointestinal disturbances such as nausea, vomiting, anorexia, and diarrhea. Central nervous system side effects such as dizziness, weariness and drowsiness frequently occur. Erythema multiforme, a condition characterized by vivid red lesions of the skin of the face, neck, forearms, legs and dorsal surfaces of the hands and feet, has also been associated with thiabendazole therapy.

Thus, the thioureylenes and thiabendazole are relatively non-toxic agents which have been used in various therapies for years and whose side effects are well known. There is a need to develop new uses for these drugs, especially for the treatment of conditions such as psoriasis and autoimmune disorders where no satisfactory therapy has yet been developed.

SUMMARY OF THE INVENTION

In accordance with one aspect of the present invention, there is provided a method of minimizing or treating psoriasis. This method comprises identifying a patient having psoriasis and administering a thioureylene compound to the patient in an amount sufficient to reduce the symptoms of psoriasis. Types of psoriasis responsive to the therapeutic treatment in accordance with the present invention include p. annularis, p. arthropathica, p. buccalis, p. discoidea, p. figurata, flexural psoriasis, p. follicularis, guttate psoriasis, p. gyrata, inverse psoriasis, p. inveterata, p. linguae, p. ostracea, p. palmaris et plantaris, pustular psoriasis, p. rupioides, p. universalis, small plaque psoriasis, and large plaque psoriasis.

Administration of the thioureylene compound may be accomplished by the systemic or topical administration of the thioureylene compound together with a pharmaceutically acceptable carrier.

In accordance with another aspect of the present invention, there is provided a method of treatment of psoriasis comprising identifying a patient having psoriasis, and administering an effective psoriasis-reducing amount of a thiabendazole compound. Types of psoriasis responsive to the therapeutic treatment in accordance with the present invention include p. annularis, p. anthropathica, p. buccalis, p. discoidea, erythrodermic psoriasis, p. figurata, flexural psoriasis, p. follicularis, guttate psoriasis, p. gyrata, inverse psoriasis, p. inveterata, p. linguae, p. ostracea, p. palmaris et plantaris, pustular psoriasis. p. rupioides, p. universalis, chronic plaque psoriasis, small plaque psoriasis, and large plaque psoriasis.

Administration of the thioureylene compound may be accomplished by the systemic or topical administration of the thioureylene compound together with a pharmaceutically acceptable carrier.

In accordance with a further aspect of the present invention, there is provided a method of treatment of autoimmune disease. This method comprises identifying a patient having an autoimmune disease and administering an effective amount of a thioureylene or thiabendazole compound for reducing the symptoms of the autoimmune disease.

Administration of the thioureylene or thiabendazole compound may be accomplished by the systemic or topical administration of the compound together with a pharmaceutically acceptable carrier.

Autoimmune disease responsive to the therapeutic treatment in accordance with the present invention include disease such as systemic lupus erythematosus, discoid lupus erythematosus, Sjogren's syndrome, autoimmune hemolytic anemia, Hashimoto's thyroiditis, pernicious anemia, autoimmune liver disease, myasthenia gravis and rheumatic disease, including such diseases and conditions as rheumatoid arthritis, mixed connective tissue disease, scleroderma, systemic sclerosis, dermatomyositis and polymyositis.

In accordance with still another aspect of the present invention, there is provided a method of treatment of transplant rejection, comprising the identification of a patient having symptoms of transplant rejection and administering an effective amount of a thioureylene or thiabendazole compound. Preferably, the administration of the compound is systemic.

Another aspect of the invention relates to a method of treating a mammalian patient having an inflammatory skin disorder. This method includes identifying a mammalian patient having an inflammatory skin disorder and administering to the patient an effective anti-inflammatory dose of a thioureylene or thiabendazole compound. Disorders that can be treated by this method include psoriasis, atopic dermatosis, and other inflammatory skin disorders associated with autoimmune function. The dose can be determined by evaluated an increase or decrease in a variety of markers. Thus, an increase in parathyroid hormone related protein (PTHrP), in interleukin-1 receptor antagonist protein (IRAP) or in the ratio of keratin components K5 and K10 to components K13 and K16 in skin of the patient that is affected with the disorder serve as markers for effective therapy. Similarly, decreases in ornithine decarboxylase (ODC) or nuclear antigen Ki67 in affected skin can serve as markers showing that an effective dose has been applied.

Thus, the present invention provides for relatively non-toxic methods for the treatment of psoriasis, autoimmune disease including rheumatic disease, and transplant rejection. These and other features and advantages of the present invention will become apparent from the detailed description of the preferred embodiments which follows, when considered together with the attached drawings and claims.

DETAILED DESCRIPTION OF THE INVENTION

Introduction

Figure 1:
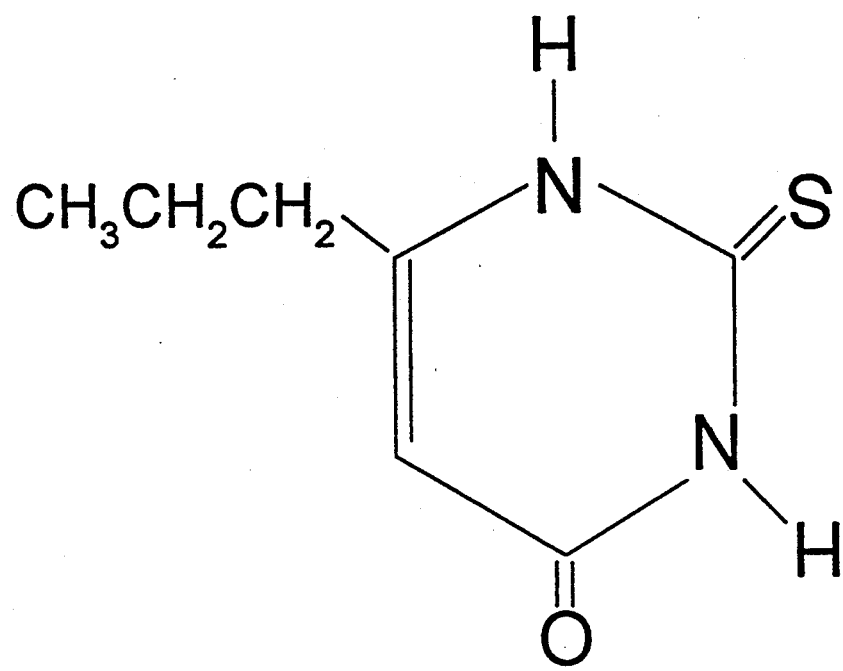
FIG. 1 shows the chemical structure of propylthiouracil.

I have discovered new uses for drugs of the thioureylene class and thiabendazole. These new uses include the treatment of psoriasis, other skin disorders and other autoimmune diseases. I have found that the immunomodulatory effects of the thioureylenes and thiabendazole are effective in treating a variety of conditions which are characterized by immune system involvement.

Accordingly, one aspect of the present invention is directed to the treatment of psoriasis and other skin disorders, such as atopic dermatosis, through thioureylene and thiabendazole therapy. Psoriasis is a disease believed to be the result of an imbalance in several factors involved in an immunological response. By way of example, and not of limitation, psoriasis diseases and conditions which can be treated using this aspect of the present invention include p. annularis, p. arthropathica, p. buccalis, p. discoidea, erythrodermic psoriasis, p. figurata, flexural psoriasis, p. follicularis, guttate psoriasis, p. gyrata, inverse psoriasis, p. inveterata, p. linguae, p. ostracea, p. palmaris et plantaris, pustular psoriasis, p. rupioides, p. universalis, chronic plaque psoriasis, small plaque psoriasis, and large plaque psoriasis.

Another aspect of the present invention is directed to the treatment of autoimmune diseases, including rheumatic disease and transplant rejection using thioureylenes and thiabendazole. By way of example, and not of limitation, diseases and conditions which can be treated using this aspect of the present invention include rheumatoid arthritis, mixed connective tissue disease, scleroderma, systemic sclerosis, dermatomyositis, polymyositis, systemic lupus erythematosus, discoid lupus erythematosus, Sjogren's syndrome, autoimmune hemolytic anemia, Hashimoto's thyroiditis, pernicious anemia, autoimmune liver disease and myasthenia gravis.

The Immune System Involvement in Psoriasis

As stated above, various factors involved in an immunological response are believed to be involved in the pathogenesis of psoriasis. These factors and their role in the development of psoriasis is described below.

Keratinocyte Proliferation by Autocrine Growth Factors and Cytokines

Transforming growth factor-alpha (TGF-$\alpha$) is a single chain peptide growth factor that binds to the same membrane-bound receptor (a-170 kDA glycoprotein with Try-PK activity) that binds epidermal growth factor (EGF). TGF-$\alpha$ has homology with the N-terminal portion of EGF. TGF-$\alpha$ is produced by normal keratinocytes and by keratinocytes maintained in culture. I believe that TGF-$\alpha$ plays an important role in maintaining the normal renewal of epidermis, and that uncontrolled production of TGF-$\alpha$ in psoriasis would result in the hyperkeratosis characteristic of this disorder.

In addition to TGF-$\alpha$, keratinocytes have been shown to synthesize a number of cytokines such as interleukin-1 (IL-1), IL-3 and IL-6 as well as colony stimulating factors (GM-CSF) and TGF-beta (TGF-$\beta$). TGF-$\beta$ tends to inhibit keratinocyte proliferation and thus tends to counteract the effects of the interleukins which are stimulatory. TGF-$\beta$ also opposes the growth promoting effect of TGF-$\alpha$, and activates the gene for parathyroid hormone related peptides (PTHrP) which also inhibit epidermal proliferation. TGF-$\beta$, with a molecular weight of $-26,000$, is a homodimer of two 112 aa chains connected by SS-bridges (9 cysteines in each chain). It does not react with the EGF receptor, but only with its own receptor. The TGF-$\beta$ receptor is formed of 2 glycosylated chains, each with a molecular weight of $-300,000$, and does not have Try-PK activity. The cytokines IL-1 and IL-6 are more potent keratinocyte growth stimulants than TGF-$\alpha$ or EGF. IL-6 receptors have been demonstrated on keratinocytes maintained in culture. These cells have an estimated 6100 binding sites per cell in contrast to 190,000 binding sites for EGF. The fewer binding sites per cell for IL-6 compared to binding sites for EGF encourages growth stimulation by IL-6 at lower molar concentrations compared to TGF-α which binds to the EGF receptors.

In addition to TGF-β, interferon-gamma (INF-γ) inhibits keratinocyte proliferation. I believe that an imbalance in the ratio of keratinocyte growth stimulating factors and inhibitors could lead to the unchecked epidermal hyperplasia seen as psoriasis.

HLA-DR expression by keratinocytes and the induction of ICAM-1 in these cells is especially dependent on γ-interferon. Keratinocyte growth factors such as EGF tend to have a limited effect on keratinocyte proliferation because of down regulation of the growth factor receptor on the keratinocyte that follows ligand binding. Keratinocytes when exposed to γ-interferon tend to have impaired down regulation of the EGF receptors which predisposes them to enhanced stimulation. I believe γ-interferon may thus play a very important role in the epidermal hyperplasia seen in psoriasis.

The immune suppressive drug, cyclosporine A has been shown to improve the clinical lesions in psoriasis. This improvement is paralleled by a corresponding decrease in the cutaneous infiltrate of T cells, macrophages and antigen-presenting cells. Analysis of the proliferating cells in the dermis in patients with psoriasis has shown that the cells consist of T cell, endothelial cells and factor XIIIa perivascular dendritic cells. I believe it likely that γ-interferon which enhances the keratinocyte growth response to growth factors such as TNF-α acting via the EGF receptor on these cells is produced by activated T cells, particularly the subclass of T cell called the recall antigen-reactive helper T cell (CD45RO+).

Adhesion Receptors and Psoriasis

T cell receptors (TCR) recognize antigens as peptide fragments that bind to cell-surface molecules that are encoded by the major histocompatibility complex (MHC). T lymphocytes are activated by specific binding of their receptors to the peptide-MHC complexes which are present on the surface of antigen-presenting cells such as macrophages. The MHC molecules that present antigens for recognition by TCRs consist of 2 structurally distinct classes. Of these MHC class I molecules bind to peptides derived from endogenously synthesized molecules such as viral proteins in infected cells and are recognized primarily by the T cytotoxic or killer cells (NK cells). MHC class II molecules bind to peptides derived from exogenous, phagocytosed antigen and are recognized by the T helper cells. Two molecules identified by monoclonal antibodies against cell-surface molecules of T lymphocytes designated CD8 and CD4 have been shown to act as co-receptors for the class I and class II MHC molecules respectively.

In addition, T cells possess surface molecules termed by lymphocyte-function associated antigens (LFA) of which 3 have been identified by monoclonal antibodies. These LFAs have been designated LFA-1, LFA-2 (CD2) and LFA-3. I believe that these molecules are responsible for the localization (recruitment) of activated T cells to sites of antigen accumulation in vivo.

LFA-1 is a member of the integren family of immunoglobulins that is expressed on T lymphocytes. Its counter receptors are the intercellular adhesion molecules ICAM-1 and -2. Unlike IFA-1 which is restricted to leukocytes, ICAM-1 is expressed by a wide variety of cells and its induction in such cells is an important means of regulating IFA-1/ICAM-1 interactions. In the absence of a pathological response (e.g., inflammation), ICAM-1 is expressed in only a few cells. Inflammatory mediators such as IL-1, TNF-α, γ-INF cause strong induction of ICAM-1 in a wide variety of tissues and greatly promote aggregation in these tissues by IFA-1 expressing lymphocytes and monocytes. The type of cell (epithelial, endothelial, fibroblast, etc.) determines which particular cytokine or group of cytokines is capable of causing ICAM-1 expression in that particular cell. In psoriasis there is enhanced expression of ICAM-1 on vascular endothelium and keratinocytes.

Interleukin-1 Receptor Antagonist Protein (IRAP)

Normal human epidermis exhibits the presence of material that is identifiable as interleukin-1, in both alpha and beta forms (IL-1α and IL-1β). Recently, work from several laboratories has culminated in the isolation and cloning of an IL-1 receptor protein which inhibits IL-1 activity. This material called IL-1 receptor antagonist protein (IRAP) has a molecular mass of 18–33 kDa, and has significant homology to IL-1α and IL-1β. Keratinocytes maintained in culture have been reported to produce IRAP. The co-localization of IL-1 and its inhibitory peptide in normal epidermis suggests the existence of an IL-1-based regulatory mechanism in keratinocyte turnover and maturation. Kristensen et al. have recently shown that IRAP expression in psoriatic lesions is decreased. Reduction in IRAP in psoriasis could thus be responsible at least in part for the IL-1-dependent epidermal hyperproliferation seen in psoriasis. Thus, an increase in IRAP is believed to serve as a marker for effective anti-psoriasis activity.

Inhibitory Factors in Psoriasis—TGF-β and PTHrP

Parathyroid hormone related protein (PTHrP) is produced by normal keratinocytes and has been localized to several tissues most of which are either epidermal or neuroectodermal in origin, such as breast, central nervous system, pituitary gland or pancreatic islets. Three structurally related PTHrP isoforms can be generated by alternate splicing of the PTHrP gene transcript. Th amino acid sequence of PTHrP shows dissimilarity to PTH except for significant homology (70%) to PTH at amino acids 1–13 of the N-terminal region of the molecule. PTHrP is believed to play an important physiological role in maintaining the fetal-material calcium gradient, and is the cause in many instances of hypercalcemia of malignancy. Moroever, PTHrP has been shown to function as an autocrine inhibitor of lymphocytes.

The gene for PTHrP is activated by transforming growth factor beta (TGF-β). Five distinct gene products, designated $TGF-β_1$ through $TGF-β_5$, comprise the TGF-β family. TGF-β, unlike other growth factors, such as TGF-α, tends to inhibit cell growth. TGF-β has been reported to promote PTHrP gene transcription by activation of exon number 6 in the human PTHrP gene located on chromosome number 11.

In view of the foregoing, I believe that PTHrP exerts an inhibitory effect on keratinocyte growth and differentiation. Thus, a lack of PTHrP could lead to the epidermal proliferation seen in psoriasis. One explanation for the beneficial effects of anti-thyroid thioureylenes in psoriasis is that these compounds enhance PTHrP production in affected skin. Thus, an increase in PTHrP is believed to serve as a marker for effective anti-psoriasis activity.

Markers of Epidermal Proliferation

Ornithine decarboxylase (ODC) is a marker of epidermal growth and proliferation. ODC is a rate-limiting enzyme in the synthesis of polyamines, which are required for DNA synthesis. Enhanced ODC activity, therefore, correlates with enhanced epidermal proliferation. Thus, a decrease in ODC activity is believed to serve as a marker for effective anti-psoriasis activity.

Epidermal proliferation is also associated with enhanced expression of the nuclear antigen Ki67 and certain subtypes of keratin, such as K13 and K16, relative to the keratin components K5 and K10. The latter components are in greater abundance in non-proliferating epidermis. Thus, a decrease in the ratio of K5 and K10 relative to K13 and K16, as well as a decrease in the level of Ki67, are believed to serve as markers for effective anti-psoriasis activity.

Chemotactic Components in Psoriatic Scales

A strongly chemotactic component is present in psoriatic scales. This material was isolated using ion exchange chromatography and was found to be the desarginated form of the C5 split product designated as $C5a_{des\ arg}$. This material is not found in the scales from other scaling disorders suggesting that its production is closely linked to the psoriatic process. Another factor called anionic neutrophil activating peptide has been isolated from psoriatic scales. This substance is distinct from IL-1 and is strongly chemotactic for neutrophils. The material has a molecular weight of approximately 8 kD and exhibits pronounced chemotactic activity for neutrophils but not for monocytes or eosinophils. A factor subsequently isolated from activated human T cells was found to be antigenically similar to anionic neutrophil activating peptide. Analysis of the amino acid sequence of this material from activated T cells showed it to posses homology with platelet factor 4 (connective tissue activating peptide).

Patients with psoriasis have been shown to exhibit elevated levels of IL2R concentrations in their serum which is presumed to reflect enhanced T-cell activation in these patients. I believe that the presence of an increased number of activated T lymphocytes in psoriatic skin also suggests an important role for the immune system in the pathogenesis of the disorder.

The various epidermal cell derived cytokines that I believe are possibly involved in psoriasis are listed in Table 1.

TABLE 1

EPIDERMAL CELL DERIVED CYTOKINES

A. Non-specific multifunctional mediators
   Interleukin-1α and -β
   Interleukin-6
   Tumor necrosis factor-α
B. Leukocyte stimulating factor
   Interleukin-8
C. Colony stimulating factors (CSF)
   Interleukin-3 (multi-CSF)
   Granulocyte-macrophage CSF
   Granulocyte CSF
   Macrophage CSF
D. Growth factors
   Transforming growth factor-α-β
   Basic fibroblast growth factor
   Platelet derived growth factor
E. Suppressor factors
   Contra-interleukin-1
   Keratinocyte lymphocyte inhibitory factor (transforming growth factor-β)
   Parathyroid hormone related peptides
   Interleukin-1 receptor antoagonist protein In view of the known immune modulatory effects of thioureylenes and the immune system involvement in the pathogenesis of psoriasis and autoimmune disorders, including rheumatoid arthritis, and transplant rejection, I decided to investigate the effects of this class of drugs on patients with these diseases. As a result, I have discovered new, less toxic methods of treatment for psoriasis and other diseases characterized by immune system involvement as will be described below.

For the treatment of psoriasis and various autoimmune disorders, the thioureylenes and thiabendazole can be administered orally, topically, or parenterally. The term "parenteral" as used herein includes all non-oral delivery techniques including transdermal administration, subcutaneous injection, intravenous, intramuscular, intravascular and intradermal injection, or infusion techniques. The term "systemic" as used herein includes all oral and parenteral delivery techniques.

The dosage administered depends primarily on the specific formulation and on the object of the therapy. The amount of individual doses as well as the administration is best determined by individually assessing the particular case. However, in preferred compositions, the dosages of thioureylenes or thiabendazole per day are preferably in the range of 0.01 mg/kg total body mass to 100 mg/kg total body mass, more preferably in the range of 0.1 mg/kg total body mass to 10 mg/kg total body mass.

The pharmaceutical compositions containing the active ingredient may be in a form suitable for oral use, for example as tablets, pills, capsules, gel caps, troches, lozenges, aqueous or oily suspensions, dispersible powders or granules, or syrups or elixirs. The amount of active ingredient that may be combined with carrier materials to produce a single dosage form will vary depending upon the patient treated and the particular mode of administration.

For injection, the therapeutic amount of thioureylene or thiabendazole or their pharmaceutically acceptable salts will normally be made by subcutaneous or intradermal injection. The pharmaceutical compositions for parenteral administration will contain active ingredient in a carrier solution. Several such carrier solutions are well known to those of skill in the pharmaceutical arts.

A composition for topical application or infusion can be formulated as an aqueous solution, lotion, cream, jelly or an oily solution or suspension. A composition in the form of an aqueous solution is obtained by dissolving the thioureylene or thiabendazole in aqueous buffer solution, and, if desired, adding a polymeric binder. An oily formulation for topical application is obtained by suspending the thioureylene or thiabendazole in an oil. Such formulations will be readily apparent to those skilled in the art.

PROPYLTHIOURACIL THERAPY

One particular thioureylene, propylthiouracil (PTU), is frequently used as first line treatment of patients with hyperthyroidism. The chemical structure of PTU is illustrated in FIG. 1. In view of the immune modulatory effects of propylthiouracil and its frequent use in anti-thyroid therapy, I decided to first study the therapeutic response of patients with psoriasis to PTU. As discussed below, I have discovered that PTU is effective in the treatment of psoriasis. Patients with chronic psoriasis receiving eight weeks of PTU treatment showed a significant resolution of their psoriatic plaques.

I began by identifying patients to participate in the study. I wished to study only those patients suffering from chronic psoriasis. Clinical evaluation of the patients was performed to evaluate their condition prior to the start of propylthiouracil therapy. Selection and evaluation of the patients is explained below in Example 1.

EXAMPLE 1

Selection and Clinical Evaluation of Patients

Ten patients (seven men, three women) suffering from chronic psoriasis were enrolled in the study. The patients ranged in age from 26–72 years (mean ±SE, 50.0±5.9). The mean duration of the disease was 24.8±4.5, range 8 to 50 years). The types of psoriasis seen in the patients were: 1 guttate, 3 small plaque, 5 large plaque, and one patient with primarily hand/foot involvement. None of the patients had received photo or systemic therapy for their psoriasis for at least four weeks prior to the start of the study, and none had used topical therapy other than emollients for two weeks prior to entry into the study. During the study, emollients were the only topical treatment allowed. Other exclusion criteria included a known allergy to sulfa, history of hypothyroidism, and pregnancy.

Prior to study, each patient had a complete blood count (CBC), and blood was also removed for measurement of thyroid stimulating hormone (TSH). A pregnancy test (serum $\beta$-HCG) was obtained in female patients of child-bearing age; patients testing positive were excluded from the study.

Clinical evaluation of the patients was performed independently by two dermatologists. Initial clinical assessment included a determination of the Psoriasis Areas Severity Index (PASI) for each patient. Clinical assessment of the psoriatic plaques was made using a scoring system based on total body surface area involved (rule of 9's), amount of scale, degree of erythema, and thickness of the psoriatic plaques. The scores range from 0–4 (0=absent; 1=slight; 2=moderate; 3=severe; 4=very severe).

Punch biopsies from an area of involved psoriatic skin were obtained at the beginning of the study. The biopsies were reviewed by a dermatopathologist who was blind to the source of the specimen and to whether the specimen was pre- or post-treatment with PTU. Histological scoring was made using a 5-point grading system (0-4) after examination of four consecutive high-power fields. Histological scoring was based on epidermal hyperplasia, degree of hypogranulosis, degree of parakeratosis, and the intensity of the inflammatory infiltrate in the epidermis and superficial layers of the dermis.

Once the patients had been selected and their condition evaluated, propylthiouracil therapy was begun. Therapy continued for 8 weeks, after which clinical evaluation was repeated for all patients, as explained below in Example 2.

EXAMPLE 2

PTU Treatment and Post-Treatment Clinical Evaluation of Patients

Patients were instructed to take propylthiouracil (Lederle Laboratories, Wayne, N.J.), 100 mg every eight hours, for the next eight weeks. Blood was removed every two weeks in order to monitor thyroid function. A CBC was again obtained in each patient at the conclusion of the study.

Clinical and Histological Assessment of Psoriasis:

Clinical evaluation of the patients was performed independently by two dermatologists at two week intervals until the end of the study. At each visit the Psoriasis Areas Severity Index (PASI) was determined for each patient as described in connection with Example 1.

Punch biopsies from an area of involved psoriatic skin were obtained from an area adjacent to the initial biopsy site. The biopsies were reviewed by a dermatopathologist who was blind to the source of the specimen and to whether the specimen was pre- or post-treatment with PTU. Histological scoring was made following the same procedure described above in Example 1.

Statistical analysis of the results of the pre- and post-PTU therapy clinical and histological evaluations was performed using ANOVA (repeated measures design). Where significant by ANOVA, data were further analyzed using Student's t-test for paired observations.

Results:

Of the 10 patients that enrolled in the study three withdrew from the study. One patient developed a hypersensitivity skin rash probably due to the medication; when the medication was discontinued, the eruption resolved. The second patient discontinued PTU on his own and began applying potent topical steroids after four weeks because he felt that his psoriasis was not responding to PUT. The third patient withdrew from the study for personal reasons. Scores are reported only for those who completed the study.

Figure 2:
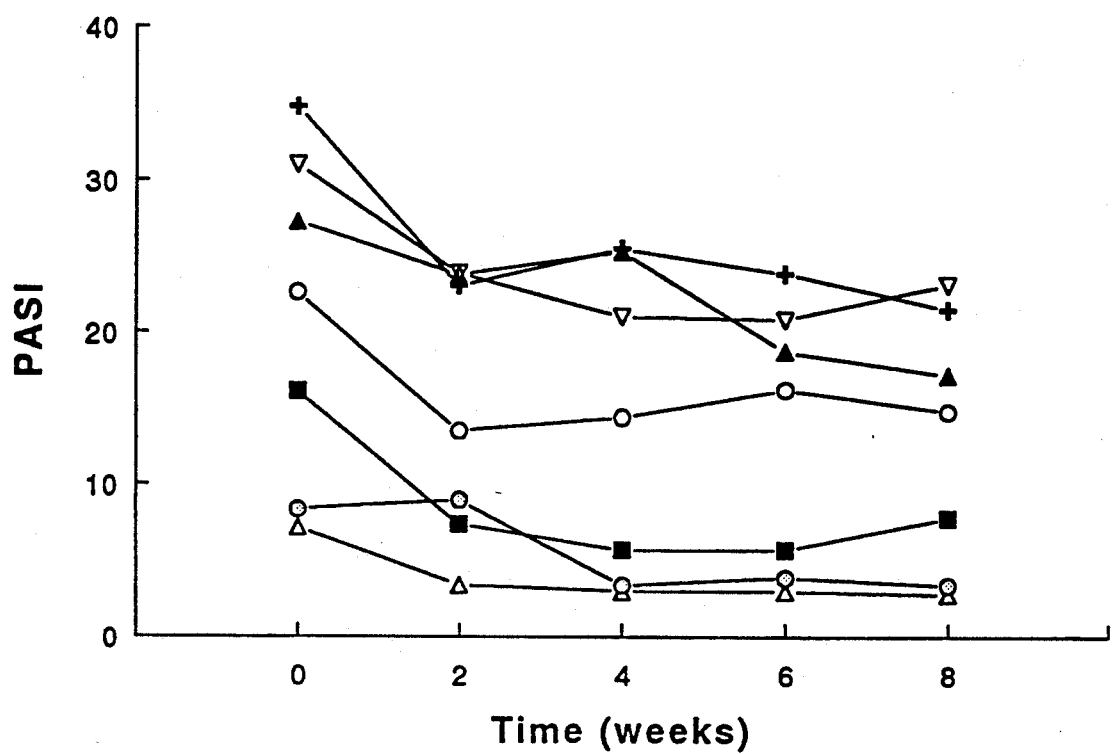
FIG. 2 is a line graph listing on the horizontal axis, the time, in weeks, of propylthiouracil (PTU) therapy. The vertical axis depicts the Psoriasis Areas Severity Index (PASI) for 7 patients with psoriasis. This graph shows improvement in the PASI for each of the patients during treatment with PTU.
Figure 3:
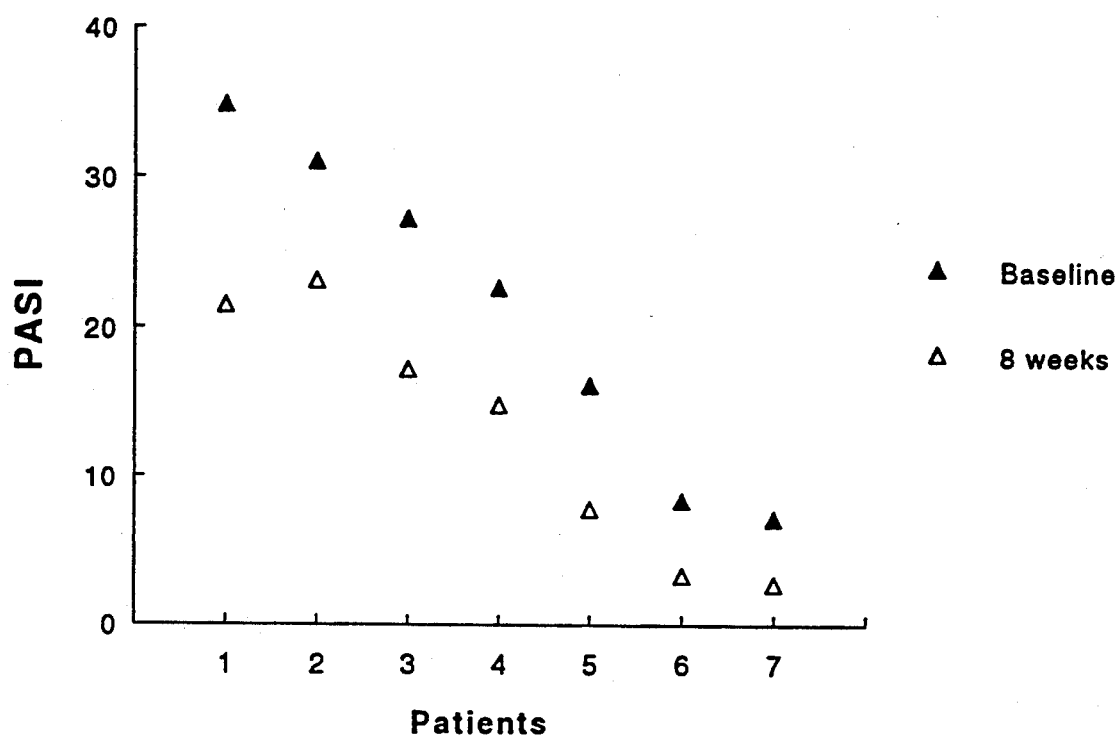
FIG. 3 is a graph depicting the PASI in individual patients with psoriasis at the start (closed triangles) and end (open triangles) of PTU therapy. The horizontal axis lists the individual patients, while the vertical axis depicts the PASI. This graph shows the improvement in the PASI of the patients over the treatment period.

Clinical Scores:

Clinical scores (PASI) are shown in FIG. 2 for each of the seven patients that remained in the study for its two month duration. FIG. 2 illustrates the improvement in the condition of each patient after receiving PTU therapy. In each patient there was a significant decline in the PASI score as shown in FIG. 3. In two patients (1 large plaque, 1 guttate) there was near-complete resolution of their psoriasis. The most consistent improvement in the psoriasis was decrease in thickness and scaling. Most patients also reported a significant decrease in discomfort and itch of their plaques. The PASI score in the group as a whole fell from an initial value of 21.04±4.10 to 12.95±3.16 (p<0.004, paired t-test).

Figure 4:
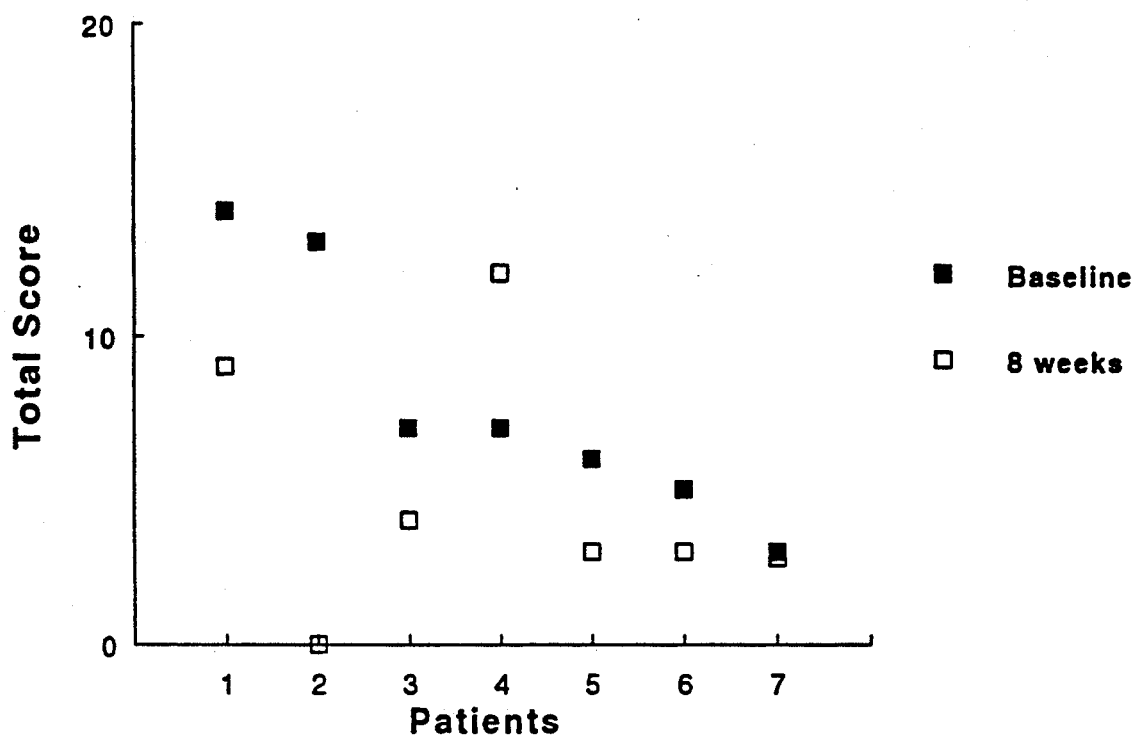
FIG. 4 is a graph depicting the histological scores in 7 patients with psoriasis at the start (closed squares) and end (open squares) of PTU therapy. This graph shows improvement in 6 of the 7 patients with PTU.

Histological Scores:

The histological scores of each patient are shown in FIG. 4. The histological scores are reported separately for epidermal thickness measured from the stratum corneum to the base (dermoepidermal junction) of the rete ridge, and as combined scores (grade 0-4) derived from separate scoring of parakeratosis, inflammatory infiltrate in the epidermis, severity of dermal infiltration, and degree of hypogranulosis. In patients in whom a particular element was not available for scoring, in either the pre-or post-treatment biopsy specimen, the score reported represents the residual score using matching parameters from pre- and post-treatment.

Epidermal thickness was not significantly reduced by PTU therapy. Pre-treatment and post-treatment epidermal thicknesses were 0.45±0.10 and 0.39±0.07 mm respectively (P=0.06, Mann-Whitney U test). However, in 2/7 patients there was greater than 30% reduction in epidermal thickness post-treatment, and scores based on the remaining scoring parameters did show a significant fall in 6/7 patients-8.00±1.83 pre-treatment, to 3.67±1.20 post treatment (P<0.03). In one patient, PTU therapy worsened the histological score (pretreatment of 7 to post-treatment of 12).

Thus, Example 2 shows that the treatment of patients with 300 mg of propylthiouracil daily for eight weeks produced a significant resolution of their psoriatic plaques as assessed by standard clinical and histological scoring of the lesions. We not wishing to be bound by any particular theory, I believe that the resolution of the psoriatic plaques is related to effects of PTU on the immune system. The fact that density of lymphocyte infiltrate in the skin biopsies from patients in the present study decreased with PTU therapy, at least in some patients, suggests that the drug is acting by preventing T-cell recruitment as well as activation. If, as in Graves' disease, the drug prevents activation and recruitment of T cells to the skin, it is a most efficient therapy for psoriasis since it acts at one of the earliest hypothesized events in the pathogenesis of the psoriatic plaque.

In addition, I believe that part of the salutary effect of PTU in psoriasis may also reside in its ability to act as a free radical scavenger. This ability would limit intradermal reactions triggered by free radicals, would attenuate free radical dependent T-cell activation and could account in part for the immunomodulatory effect of PTU.

Because of the known anti-thyroid effects of PTU, I decided to evaluate the side effects of PTU therapy on the patients in the study. This evaluation is shown below in Example 3

EXAMPLE 3

Evaluation of Side Effects of PTU Therapy

I asked the patients involved in the study to report any effects experienced during PTU therapy. In general, the medication was well tolerated. The most consistent adverse effect reported was a mild metallic taste that was experienced for a few minutes to hours following each dose of PTU.

Figure 5:
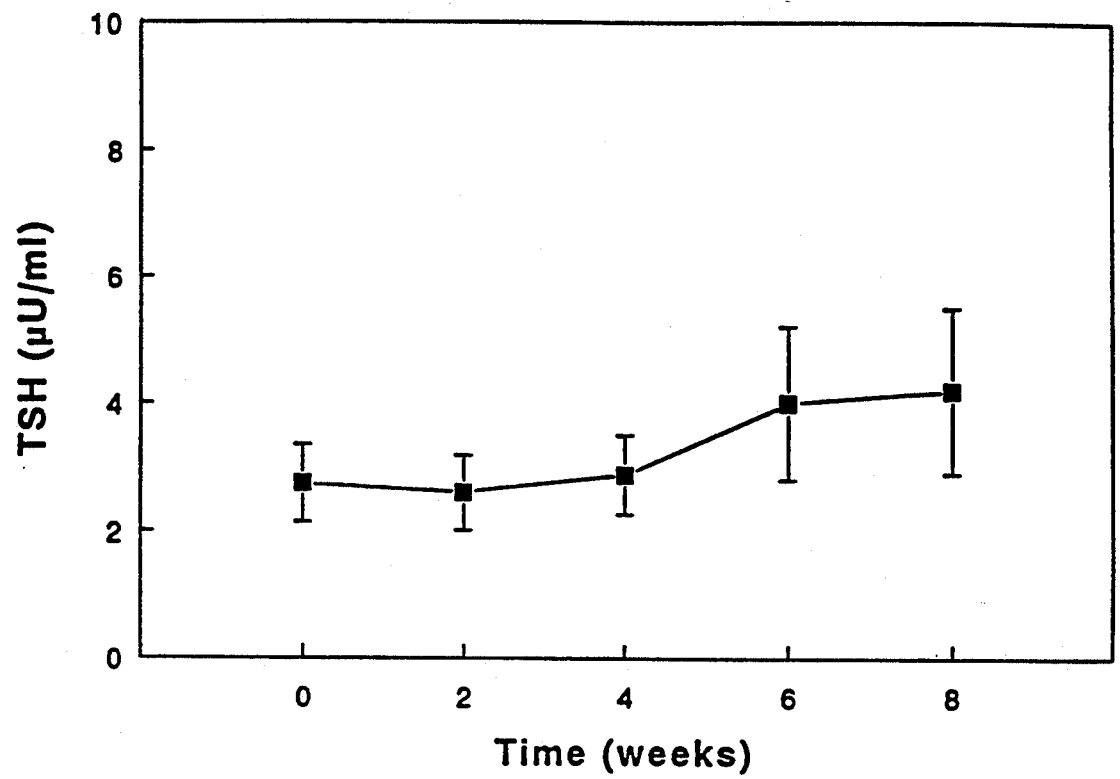
FIG. 5 is a graph depicting the thyroid stimulating hormone (TSH) concentrations in 7 patients with psoriasis treated with PTU. The horizontal axis shows the time in weeks. The vertical axis depicts the serum TSH values in $\mu U/ml$. Values are means $\pm SE$.

Thyroid Function Tests and Blood Count:

None of the patients were leukopenic at the start of the study (Total WBC count $4.3-7.0\times 10^3/mm^3$). After eight weeks of PTU therapy, WBC count did not change significantly ($4.4-6.7\times 10^3/mm^3$). As illustrated in FIG. 5, serum TSH concentration at the start of the study was $2.75\pm 1.92$ μU/ml and did not change significantly during the course of the study, except in one patient in whom TSH rose to 10.3 μU/ml (normal 0.5-5 μU/ml) at the sixth week of PTU therapy. This patient required l-thyroxine supplementation (0.1 mg daily) to restore his TSH concentration to normal (2.7 μU/ml at the close of study). At the conclusion of the study (two month interval), two other patients showed mild elevation of serum TSH to 5.5 and 5.9 μU/ml respectively.

Thus, Examples 2 and 3 demonstrate that PTU is an effective, yet non-toxic treatment for psoriasis, with very few side effects.

METHIMAZOLE THERAPY

Figure 6:
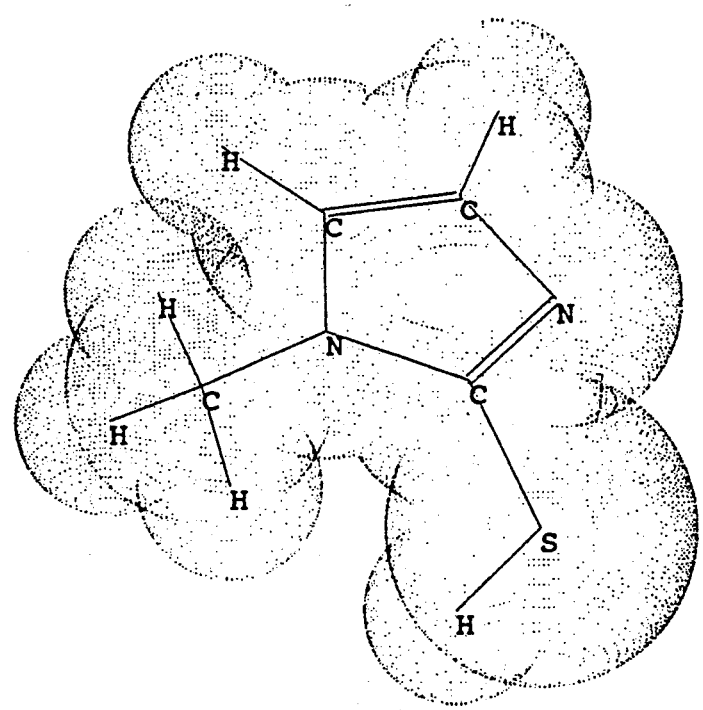
FIG. 6 is a three dimensional representation of the chemical structure of methimazole.

In view of the success in the treatment of psoriasis with PTU, I decided to investigate the effects of the related thioureylene methimazole (MMI). The chemical structure of MMI is shown in FIG. 6.

A second study was performed to determine whether MMI had similar therapeutic effects in patients with psoriasis. I began by selecting patients to participate in the study. Again, I wished to study only those patients suffering from chronic psoriasis. Clinical evaluation of the patients was performed to evaluate their condition prior to the start of methimazole therapy. Selection and evaluation of the patients is explained below in Example 4.

EXAMPLE 4

Selection and Clinical Evaluation of Patients

Eight patients (5 men, 3 women) suffering from chronic psoriasis were enrolled in the study. The patients ranged in age from 30-56 years (mean±SE, 40.1±3.3). The mean duration of the disease was 22.9±4.2, range 14 to 50 years). The types of psoriasis seen in the patients were: 3 guttate, 1 small plaque, 4 large plaque. None of the patients had received photo or systemic therapy for their psoriasis for at least 4 weeks prior to the start of the study, and none had used topical therapy other than emollients for 2 weeks prior to entry into the study. During the study, emollients were the only topical treatment allowed. Other exclusion criteria included a known allergen to sulfa, history of hypothyroidism, and pregnancy.

Prior to study, each patient had a complete blood count (CBC) and blood was also removed for measurement of thyroid stimulating hormone (TSH). A pregnancy test (serum β-HCG) was obtained in female patients of child-bearing age; those patients testing positive were excluded from the study.

Clinical evaluation of the patients was performed independently by 2 dermatologists. Initial clinical assessment included a determination of the Psoriasis Areas Severity Index (PASI) for each patient. Clinical assessment of the psoriatic plaques was made using a scoring system based on total body area involved (rule of 9's), amount of scale, degree of erythema, and thickness of the psoriatic plaques. The scores range from 0-4 (0=absent; 1=slight; 2=moderate; 3=severe; 4=very severe).

Punch biopsies from areas of involved psoriatic skin were obtained at the beginning of the study. The biopsies were reviewed by a dermatopathologist who was blind to the source of the specimen and to whether the specimen was pre-or post-treatment with methimazole. Histological scoring was made using a 5-point grading system (0-4) after examination of 4 consecutive high-power fields. Histological scoring was based on epidermal hyperplasia, degree of hypogranulosis, degree of parakeratosis, and the intensity of the inflammatory infiltrate in the epidermis and superficial layers of the dermis. The scores reported were a composite of the scores for each parameter, such as degree of hyperkeratosis, used in the scoring system.

Once the patients had been selected and their condition evaluated, methimazole therapy was begun. Therapy continued for 8 weeks, after which clinical evaluation was repeated for all patients, as explained below in Example 5.

EXAMPLE 5

MMI Treatment and Post-Treatment Clinical Evaluation of Patients

Patients were instructed to take methimazole (Eli Lilly Co., Indianapolis, Ind.), 20 mg every twelve hours, for the next 8 weeks. Blood was removed every 2 weeks in order to monitor thyroid function. A CBC was obtained again in each patient at the conclusion of the study.

Clinical and Histological Assessment of Psoriasis:

Clinical evaluation of the patients was performed independently by 2 dermatologists at 2 weeks intervals until the end of the study. At each visit the Psoriasis Areas Severity Index (PASI) was determined for each patient as described above in connection with Example 4.

Punch biopsies from areas of involved psoriatic skin were obtained from areas adjacent to the initial biopsy sites. The biopsies were reviewed by a dermatopathologist who was blind to the source of the specimen and to whether the specimen was pre- or post-treatment with methimazole. Histological scoring was made following the same procedure described in connection with Example 4. The scores reported were a composite of the scores for each parameter, such as degree of hyperkeratosis, used in the scoring system.

Statistical analysis of the results of pre- and post-MMI therapy clinical and histological evaluations was performed using ANOVA (repeated measures design). Where significantly by ANOVA, data were further analyzed using Student's t-test for paired observations, and non-parametric tests (Mann-Whitney U test).

Clinical Scores

Figure 7:
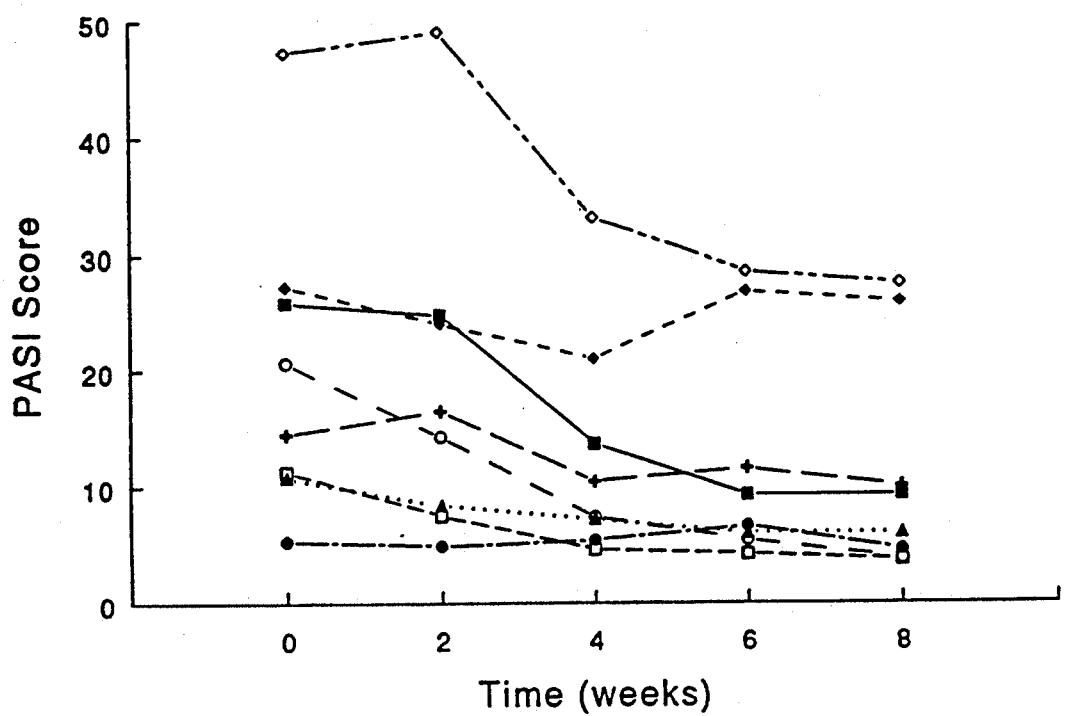
FIG. 7 is a line graph listing on the horizontal axis, the time, in weeks, of methimazole (MMI) therapy. The vertical axis depicts the Psoriasis Severity Areas Index (PASI) for 8 patients with psoriasis. This graph shows improvement in the PASI for each of the patients during treatment with MMI.
Figure 8:
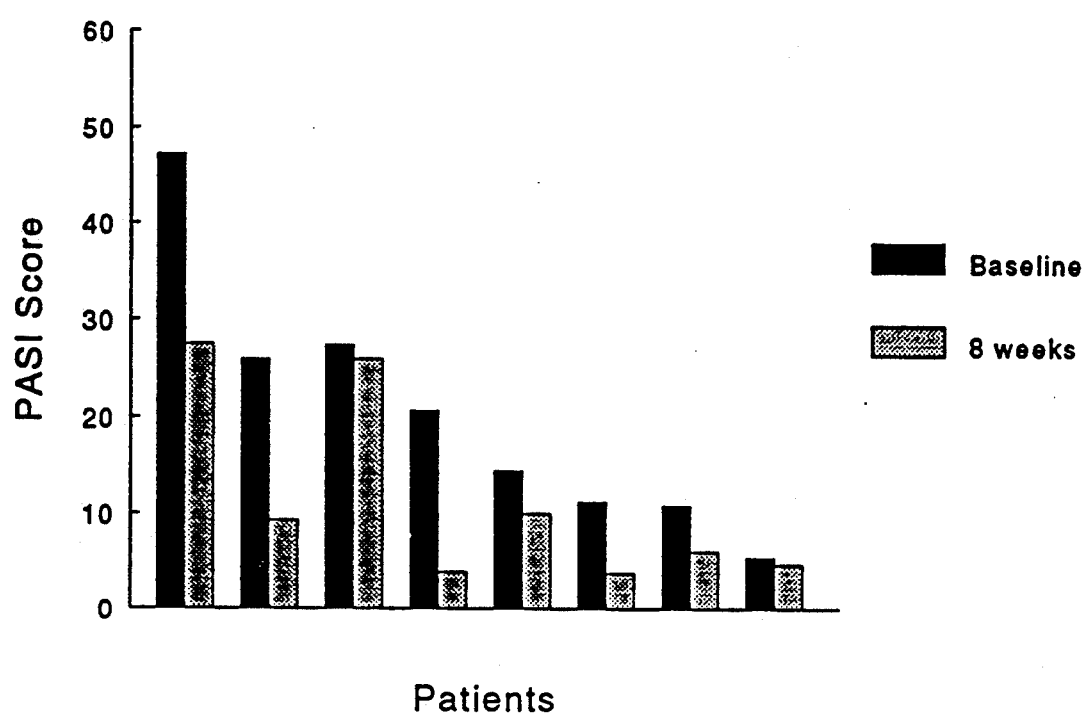
FIG. 8 is a bar graph depicting the PASI in individual patients with psoriasis at the start (solid bar) and end (shaded bar) of MMI therapy. The horizontal axis lists the individual patients, while the vertical axis depicts the PASI. This graph shows the improvement in the PASI of the patients over the treatment period.

Individual clinical scores (PASI) for each of the 8 patients in the study are shown in FIG. 7 and FIG. 8. In each patient there was a decline in the PASI score indicating an improvement in their condition. The most consistent improvement in the psoriasis was decrease in thickness and scaling. Most patients also reported a significant decrease in discomfort and itch of their plaques. The PASI score in the group as a whole fell from an initial value of $20.4 \pm 4.7$ to $11.4 \pm 3.5$ ($p<0.02$, paired t-test). One patient who showed improvement in his PASI score, which fell from 27.3 to 20.9 after 4 weeks of therapy, relapsed during the second month so that his final PASI score was at 25.9. This patient experienced personal stress at the time preceding his relapse.

Histological Scores

Figure 9:
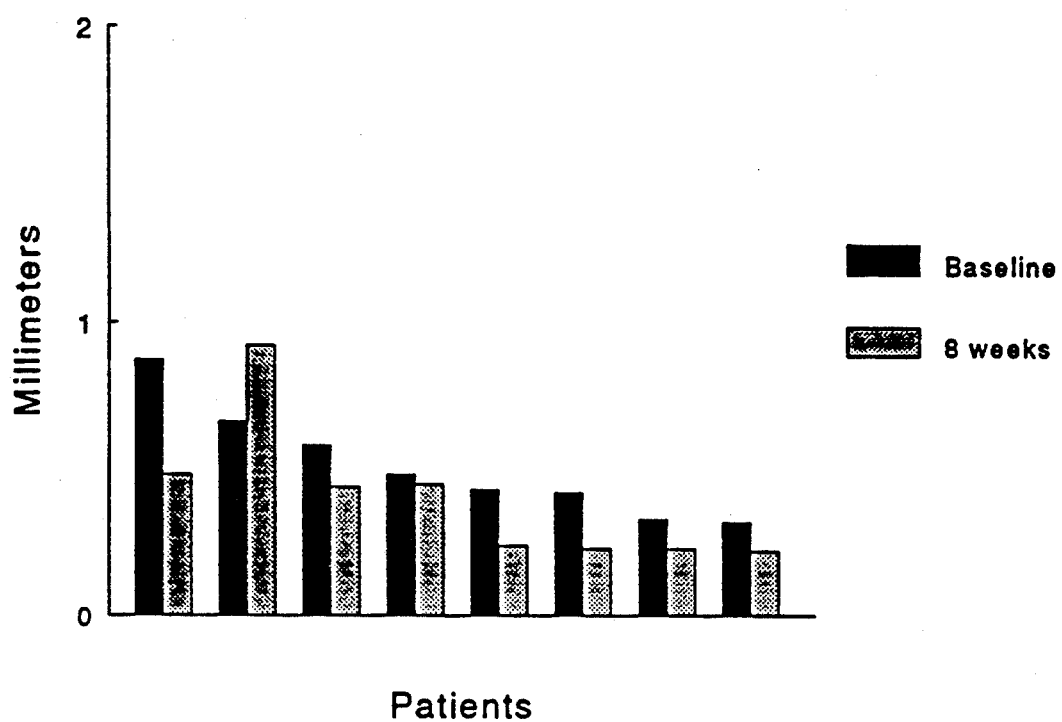
FIG. 9 is a bar graph depicting the epidermal thickness in individual patients with psoriasis at the start (solid bar) and end (shaded bar) of MMI therapy. The horizontal axis lists the individual patients, while the vertical axis depicts the thickness, in millimeters, of the epidermis. This graph shows the improvement in the epidermal thickness in 7 of 8 patients over the treatment period.

The histological scores are reported separately for epidermal thickness measured from the stratum corneum to the base (dermoepidermal junction) of the rete ridge, and as combined scores (grade 0–4) derived from separate scoring of parakeratosis, inflammatory infiltrate in the epidermis, severity of dermal infiltration, and degree of hypogranulosis. FIG. 9 depicts the scores of the individual patients.

Figure 10:
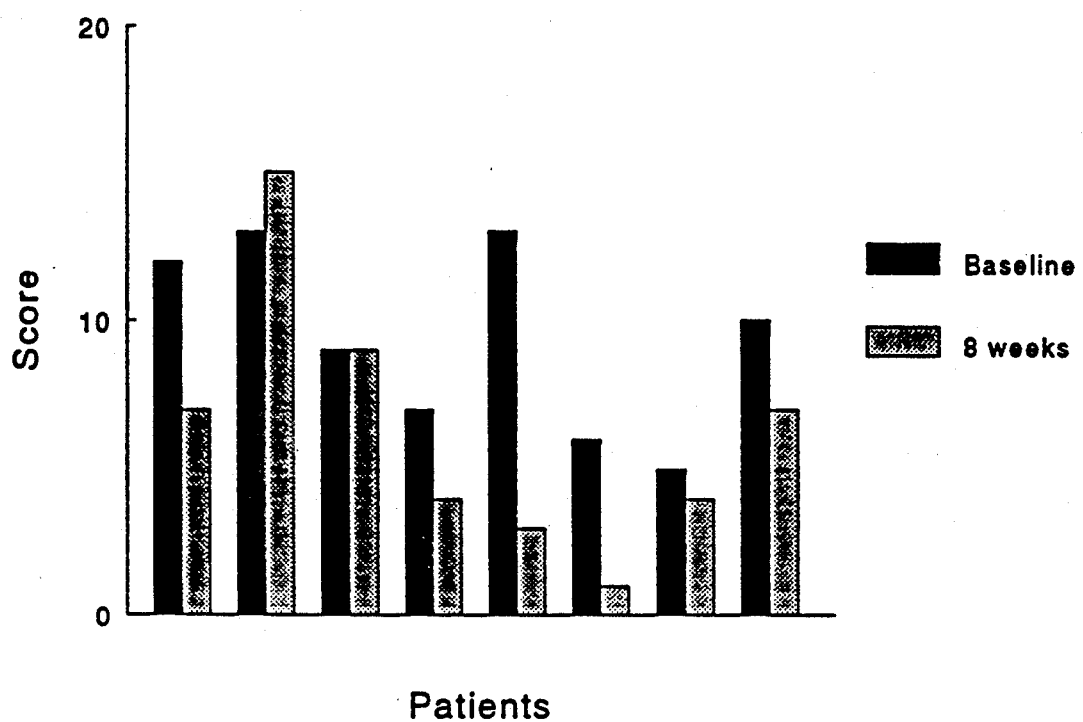
FIG. 10 is a bar graph depicting the histological scores in 8 patients with psoriasis at the start (solid bar) and end (shaded bar) of MMI therapy. This graph shows improvement in 6 of the 8 patients treated with MMI.

As seen in FIG. 9, epidermal thickness in the group as a whole was not significantly reduced by MMI therapy. Pre-treatment and post-treatment epidermal thicknesses were $0.51 \pm 0.07$ and $0.40 \pm 0.08$ mm respectively ($P=0.11$, Mann-Whitney U test). However, in 7/8 patients there was a reduction in epidermal thickness post-treatment. By excluding the patient who demonstrated an increase in epidermal thickness from 0.66 to 0.92 mm, epidermal thickness post-therapy with methimazole showed significant improvement, i.e., $0.49 \pm 0.07$ mm pre-treatment, versus $0.33 \pm 0.05$ mm post-treatment, $P<0.01$. Scores based on the remaining scoring parameters showed a significant fall, i.e., $9.38 \pm 1.12$ pre-treatment, to $6.25 \pm 1.54$ post-treatment ($P<0.05$). Histological scores for individual patients are shown in FIG. 10. As can be seen, 6 of 8 patients showed significant improvement after treatment with MMI.

Example 5 shows that treatment with 40 mg of methimazole daily for 8 weeks produced significant resolution of psoriatic plaques in the majority of patients studied as assessed by standard clinical and histological scoring of the lesions.

Without wishing to be bound by any particular theory, I believe that the beneficial effect of methimazole on the psoriatic lesions is related to immune-mediated events. It is possible that the drug prevents activation and recruitment of T cells to the affected areas. However, only some patients showed a reduction in lymphocyte infiltrate on histological examination following MMI treatment. Since methimazole is also a free radical scavenger, its beneficial effects in psoriasis may be partly due to its ability to reduce the free radical stimulus for T cell activation in the affected skin. I do not, however, believe that this is the dominant mode of action of this drug.

Because of the known anti-thyroid effects of MMI, I decided to evaluate the side effects of MMI Therapy on the patients in the study. This evaluation is shown below in Example 6.

EXAMPLE 6

Evaluation of Side Effects of MMI Therapy

I asked the patients involved in the study to report any effects experienced during MMI therapy. In general, the medication was well tolerated with none of the patients reporting any side effects that could be related to the medication. Unexpectedly, none of the patients developed clinical hypothyroidism during the duration of the study, and all but one patient remained biochemical euthyroid (TSH$<5$ $\mu$U/ml).

Thyroid Function Tests and Blood Count

Figure 11:
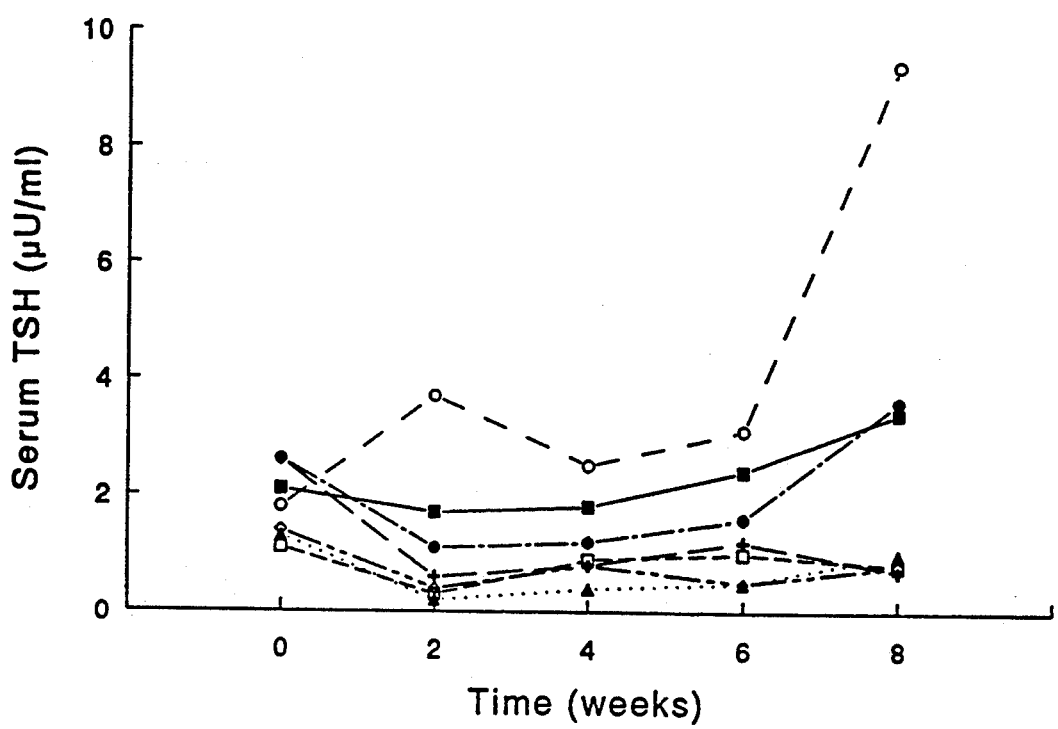
FIG. 11 is a graph depicting the thyroid stimulating hormone (TSH) concentrations in 8 patients with psoriasis treated with MMI. The horizontal axis shows the time in weeks. The vertical axis depicts the serum TSH values in $\mu$U/ml. Values are means ±SE. This graph shows that elevation into the hypothyroid range occurred in only one patient (TSH 9.4 $\mu$U/ml).

None of the patients were leukopenic at the start of the study (Total WBC count $5.0–9.8 \times 10^3$/mm$^3$). After 8 weeks of MMI therapy, WBC count did not change significantly ($6.1–9.3 \times 10^3$/mm$^3$). Serum TSH concentration at the start of the study was $1.91 \pm 0.21$ $\mu$U/ml and did not change significantly during the course of the study as shown in FIG. 11, except in one patient in whom TSH concentration at the conclusion of the study was at $9.4$ $\mu$U/ml.

Examples 5 and 6 demonstrate that MMI is an effective, yet non-toxic therapy for patients suffering from psoriasis, with few side effects.

Thus, I have shown that two members of the class of thioureylenes are effective in the treatment of psoriasis. I believe that due to their similarity, any of the drugs within the class will be as effective in resolution of psoriatic lesions.

EFFECT OF PTU AND MMI ON SERUM LEVELS OF INTERLEUKIN-2 RECEPTORS

Having demonstrated that the antithyroid thioureylene derivatives, propylthiouracil (PTU) and methimazole (MMI) when administered to patients with chronic stable plaque psoriasis were able to produce significant remission of the lesions in many of patients, I investigated the mode of action of this class of chemical compounds.

Interleukin-2 receptors (IL2R) consist of 2 distinct membrane associated IL2 binding components: and $\alpha$-subunit and a $\beta$-subunit, which are associated with in a non-covalent fashion. Soluble IL2R is released from the receptor expressed on the surface of activated T cells. Elevated levels of IL2 and IL2R have been seen in several auto-immune disorders, and tend to correlate with the clinical course of these disorders. Previous studies have shown that IL2R serum concentrations are increased in patients with psoriasis, and that some forms of therapy produce significant reduction in IL2R levels in patients with this disease.

Thus, the effect of PTU and MMI on IL2R serum concentrations in patients with plaque psoriasis before and after treatment with PTU or MMI was investigated. Since methimazole is about 10 times as potent as propylthiouracil, at least as far as its anti-thyroid effects are concerned, the dosages used in the study for each of the 2 drugs were comparable. I found that treatment with thioureylenes did not produce a significant reduction in the serum concentrations of IL2R in patients with psoriasis, thus the clinical improvement seen in these patients was due to mechanisms other than reduction in IL2R expression, and, by inference, on IL2R production. These experiments are shown in Examples 7 and 8 below.

EXAMPLE 7

Selection of Patients and Thioureylene Therapy

Fifteen patients with chronic stable plaque psoriasis were recruited for study. The patients ranged in age from 28 to 56 years (mean±SE, 42.5±3.5 years). The duration of the disease in the study population ranged from 10 to 50 years (mean±SE, 24.2±3.0 years). Blood was collected at the start of the study for measurement of IL2R in the serum. The patients were then placed on either 100 mg of PTU given every eight hours (seven patients) or MMI 20 mg twice daily (eight patients) which they took for eight weeks.

Because of the known antithyroid action of PTU and MMI, the patients were monitored for possible hypothyroidism by removal of blood for measurement of serum thyroid stimulating hormone (TSH) concentration at the start of the study. Blood was also removed for complete blood count (CBC) at the beginning of the study to monitor for thioureylene-induced cytopenia.

Clinical evaluation of all patients involved in the study was performed at the end of the 8-week therapy period. This evaluation is explained below in Example 8.

EXAMPLE 8

Clinical Evaluation of Patients Post-Thioureylene Therapy

PASI Scores:

Clinical severity of psoriasis was scored using the Psoriasis Areas Severity Index (PASI). The scoring took into account the total body surface area involved, scale, erythema and thickness of the psoriatic plaques. The scoring system utilized a 5 point score running from 0–4 (0=absent; 1=slight; 2=moderate; 3=severe; 4=very severe). PASI scores were determined for each patient at the start of the study and at two week intervals thereafter until conclusion of the study.

Measurement of Serum IL-2 Receptor:

Serum interleukin-2-receptor was measured by an enzyme-linked immunosorbent assay (ELISA) based on the use of two monoclonal antibodies recognizing two different epitopes of the heavy (alpha) chain of IL2R (Cell Free-T Cell Sciences, Inc., Cambridge, Mass.). In this assay an anti-IL2 monoclonal antibody is adsorbed onto microtiter wells. IL2R in the samples and standards is bound to the monoclonal anti-IL2 antibody in the wells. Horseradish peroxidase (HRP)conjugated anti-IL2 receptor antibody directed against a second epitope on the soluble IL2 receptor captured by the first anti-IL2 receptor antibody in the walls completed the sandwich. HRP-substrate was added to the wells and the reaction terminated by the addition of 2N $H_2SO_4$. Absorbance was read at 490 nm.

Statistical Analysis:

Data were analyzed using the Mann-Whitney U test and Student's t-test for paired and grouped observations. Level of significance was $p \leq 0.05$.

Figure 12:
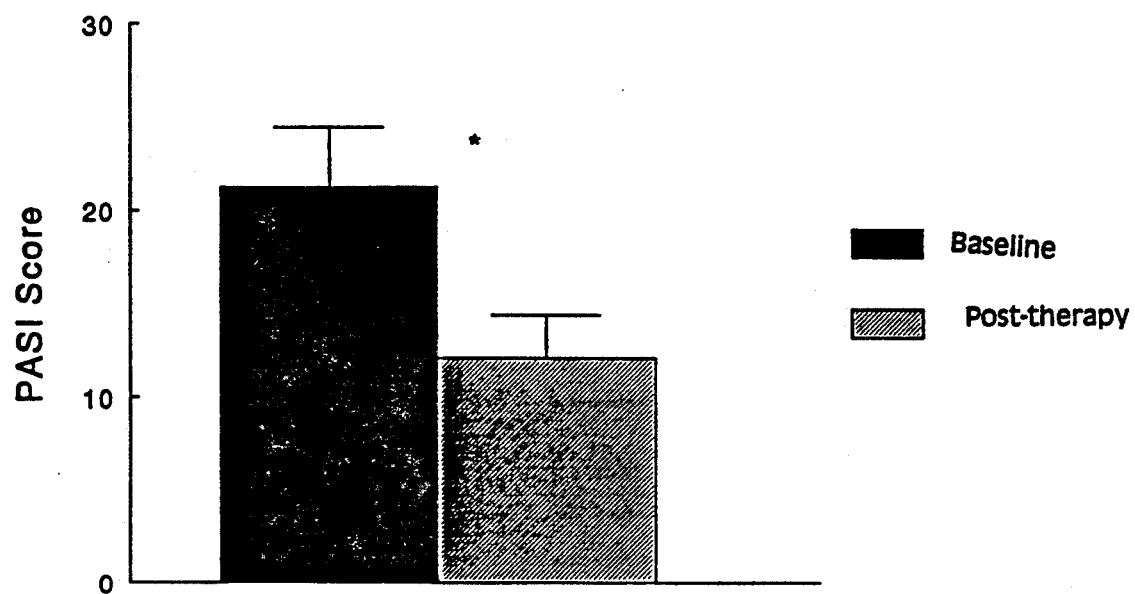
FIG. 12 is a bar graph depicting the PASI scores in 15 patients with chronic plaque psoriasis at the start (solid bar) and end (shaded bar) of treatment with either 300 mg of PTU or 40 mg of MMI daily for 8 weeks. The horizontal axis depicts the PASI score. Values are means ±SE.

PASI Scores:

PASI scores declined in all patients studied. The scores fell from baseline levels of 21.21±3.15 (mean±SE) to post-treatment levels of 12.09±2.28 ($P<0.0001$) as shown in FIG. 12.

Figure 13:
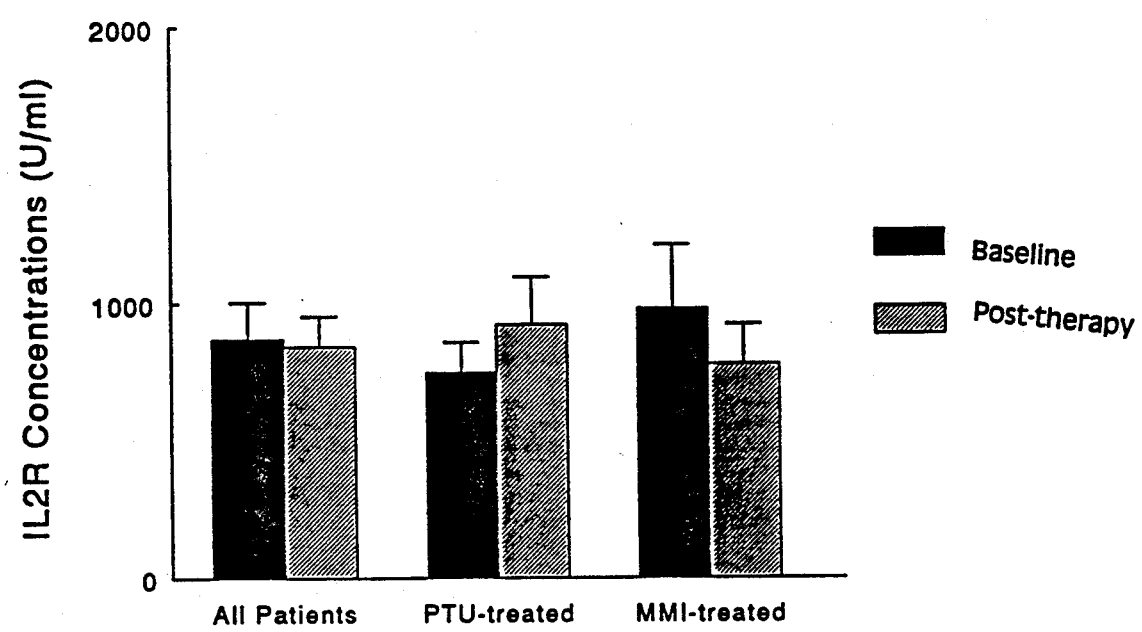
FIG. 13 is a bar graph depicting the serum interleukin-2 receptor (IL2R) concentrations at the start (solid bar) and end (shaded bar) of therapy in 7 patients treated with PTU, 8 patients treated with MMI, and all 15 patients. The horizontal axis lists the IL2R concentrations in U/ml. Values are means ±SE.

IL2R Concentrations:

Serum levels of IL2R were significantly higher in patients with psoriasis (867.33±134.65 u/ml) than in normal control volunteers (441.00±54.75 u/ml, $P<0.03$). IL2R concentrations in serum did not fall significantly in the group as a whole after treatment with PTU or MMI (867.33±134.65 u/ml baseline, versus 838.67±110.89 u/ml post-treatment, P=ns). Separate pre- and post-treatment IL2R serum concentrations in patients treated with either PTU or methimazole are shown in FIG. 13.

No significant different was found between IL2R concentrations between men and women in the control population. Serum IL2R concentrations, either in the baseline state or after treatment with thioureylenes, correlated weakly with severity of the psoriasis [r=0.42, P=0.12 (baseline), r=0.46, P=0.07 (post-therapy)] but not at all significantly with the duration of the disease [r=−0.05, P=0.85 (baseline), r=0.03, P=0.89 (post-therapy)].

As shown in Example 8, thioureylene treatment did not produce a significant reduction in the serum concentrations of IL2R in patients with psoriasis, suggesting that the clinical improvement seen in these patients was due to mechanisms other than reduction in IL2R expression and, by inference, on IL2 production.

Without wishing to be bound by any particular theory, I believe that the mechanism of action of thioureylenes in psoriasis may be distinct, at least in some ways, from other immune suppressive and immune modulatory drugs such as cyclosporine which are believed to act by influencing T cell activation by reducing mRNA coding for IL2, tumor necrosis factor and interferon gamma. The lack of strong correlation between the severity of the psoriatic plaques and their duration, and baseline IL2R serum concentrations, indicates that other mechanisms are also involved in the initial events in the pathogenesis of psoriasis, and that PTU and MMI may exert effects on these other mechanisms. Since serum thyroid hormones did not decline significantly during the study period any effect of altered thyroid hormone status on serum IL2 concentrations can be presumed insignificant.

EXAMPLE 9

Evaluation of Side Effects of Thioureylene Therapy

Because of the known anti-thyroid effects of thioureylene therapy, patients were monitored for side effects. Serum TSH concentration was measured every 2 weeks during therapy, and a CBC was performed at the end of the study to monitor for cytopenia.

None of the patients experienced any significant side effects. One patient became mildly hypothyroid while on PTU and one patient became hypothyroid while on MMI. The hypothyroidism was biochemical, as neither of these two patients complained of symptoms suggestive of clinical hypothyroidism. None of the patients developed drug-induced cytopenia which has been reported to occur in 1 in 500 to 1000 patients on antithyroid thioureylenes.

SOLUBLE ICAM-1 IN PSORIASIS

Intercellular adhesion molecule-1 (ICAM-1), a 90 kD glycosylated protein is an early marker of immune response and activation. It is the ligand that binds lymphocyte function associated antigen-1 (LFA-1) which is expressed on T cells, monocytes and neutrophils. Enhanced ICAM-1 expression on vascular endothelial cells and keratinocytes has been demonstrated in patients with psoriasis, and is believed to play an important role in lymphocyte migration and retention to the affected areas. Drugs that improve the clinical condition of patients with psoriasis can be expected to work by reducing ICAM-1 expression. Since soluble ICAM-1 is derived from cellular ICAM-1, the concentration of the soluble molecule in the serum can be used to gauge the effect of anti-psoriasis drugs on cellular ICAM-1 expression. Having previously shown that the antithyroid thioureylenes produce significant clinical improvement in patients with stable plaque psoriasis, and since ICAM-1 is an important early marker of immune activation and response, I investigated the effect of antithyroid thioureylenes on serum ICAM-1 levels in patients with psoriasis before and after 8 weeks of treatment with these medications.

I found that PTU and MMI did not reduce the serum ICAM-1 concentrations in patients with psoriasis, indicating that the effects of these thioureylenes on the clinical response of patients with psoriasis is exerted at a point distal to the early immune response characterized by enhanced ICAM-1 expression in the cellular components of the psoriatic lesions. The experiment is shown below in Examples 10 and 11.

EXAMPLE 10

Selection of Patients and Thioureylene Therapy

Fourteen patients with chronic stable plaque psoriasis were studied. The patients ranged in age from 30 to 55 years (mean $\pm$SE, 40.6$\pm$3.8 years). The duration of the disease in the study population ranged from 10 to 50 years (mean $\pm$SE, 23.7$\pm$3.3 years). Blood was removed at the start of the study for measurement of ICAM-1 in the serum. The patients were then placed on either 100 mg of PTU given every 8 hours (7 patients) or MMI 20 mg twice daily (7 patients) which they took for 8 weeks.

Because of the known antithyroid action of PTU and MMI, the patients were monitored for possible hypothyroidism by withdrawing blood from the antecubital or other forearm vein for measurement of serum thyroid stimulating hormone (TSH) concentration at the start of the study. Blood was also collected for complete blood count (CBC) at the beginning of the study to monitor for thioureylene-induced cytopenia, which is another rare side effect of the antithyroid thioureylenes.

Clinical evaluation of all patients involved in the study was performed at the end of the 8-week therapy period. This evaluation is explained below in Example 11.

EXAMPLE 11

Clinical Evaluation of Patients Post Thioureylene Therapy

PASI Scores

Clinical severity of psoriasis was scored using the Psoriasis Areas Severity Index (PASI). The scoring took into account the total body surface area involved, scale, erythema and thickness of the psoriatic plaques. The scoring system utilized a 5 point score running from 0–4 (0=absent; 1=slight; 2=moderate; 3=severe; 4=very severe). PASI scores were determined for each patient at the start of the study and at 2-week intervals thereafter until conclusion of the study.

Measurement of Serum ICAM-1 Concentration

Serum ICAM-1 was measured by an enzyme-linked immunosorbent assay (ELISA) based on the use of two monoclonal antibodies recognizing two different epitopes of the 90 kD glycosylated ICAM-1 molecule (Cell Free-T cell Sciences, Inc., Cambridge, Mass.). In this assay, an anti-ICAM-1 monoclonal antibody is adsorbed onto microtiter wells. ICAM-1 in the samples and standards is bound to the monoclonal anti-ICAM-1 antibody in the wells. Horseradish peroxidase (HRP) conjugated anti-ICAM-1 antibody directed against a second epitope on the soluble ICAM-1 molecule captured by the first anti-ICAM-1 antibody in the wells completed the sandwich. HRP-substrate and chromogen were added to the wells and the reaction terminated by the addition of 2N $H_2SO_4$. Absorbance was read at 490 nm. Sensitivity of the assay is 0.3 ng/ml. All samples were run in the same assay. With this ELISA assay, intra-assay variation ranges from 1.6 to 3% and inter-assay variation from 3.4 to 4.5%.

Statistical Analysis

Data were analyzed using the Mann-Whitney U test and Student's t-test for paired and grouped observations. Level of significance was $p \leq 0.05$.

PASI Scores

Figure 14:
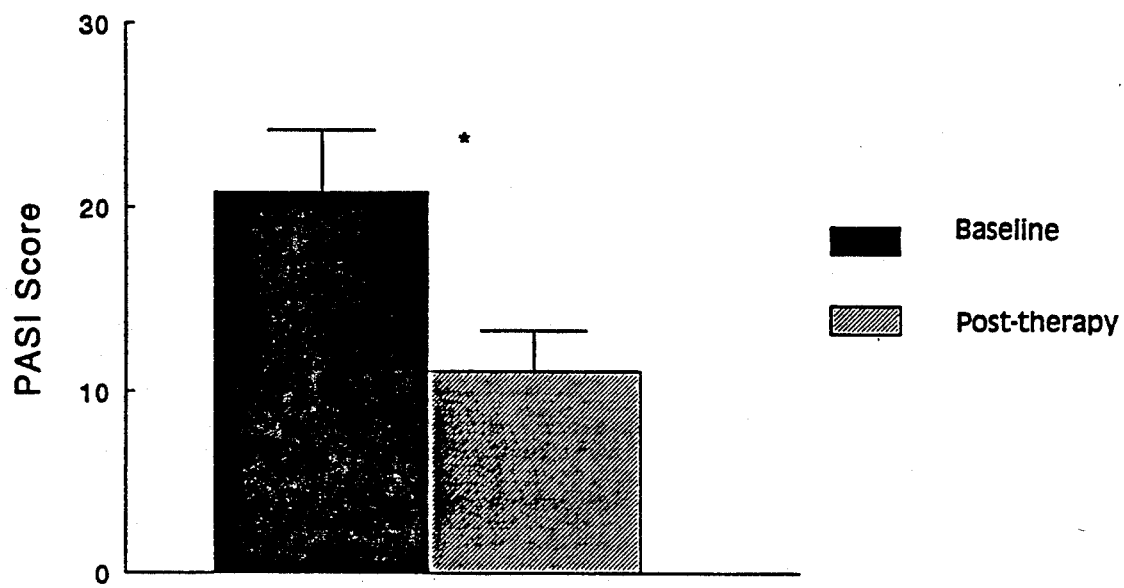
FIG. 14 is a bar graph depicting the PASI scores in 14 patients with chronic plaque psoriasis at the start (solid bar) and end (shaded bar) of treatment with either 300 mg of PTU or 40 mg of MMI daily for 8 weeks. The horizontal axis depicts the PASI score. Values are means ±SE.

PASI scores declined in all patients studied as shown in FIG. 14. The scores fell from baseline levels of 20.77$\pm$3.35 (mean $\pm$SE) to post-treatment levels of 11.11$\pm$2.21 (P<0.0001).

ICAM-1 Concentrations

Figure 15:
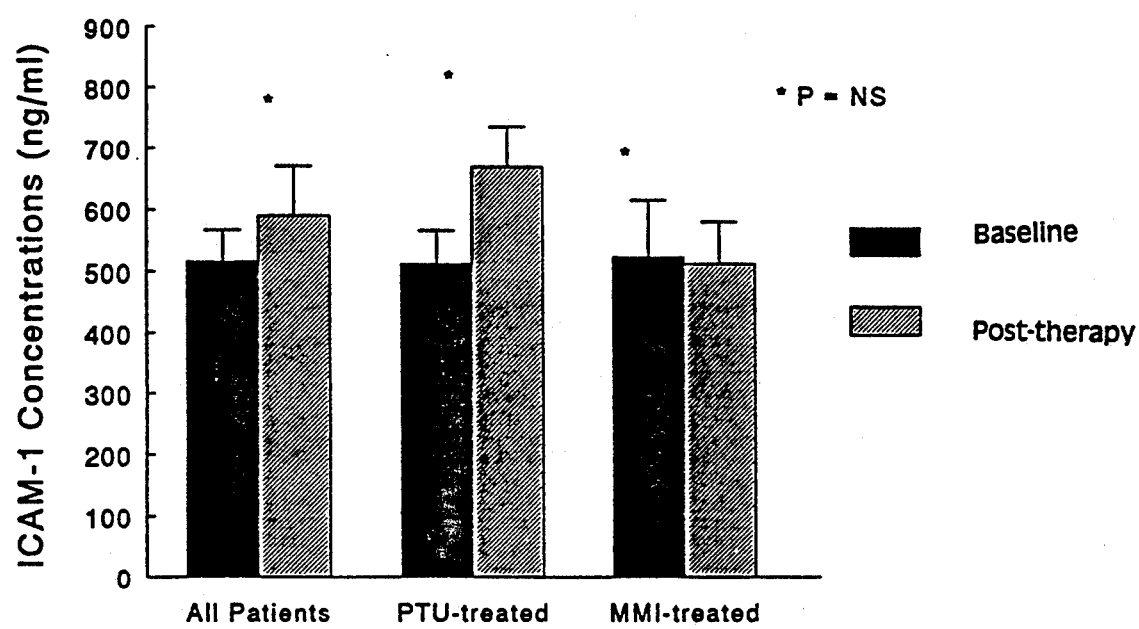
FIG. 15 is a bar graph depicting the serum intercellular adhesion molecule-1 (ICAM-1) concentrations at the start (solid bar) and end (shaded bar) of therapy in 7 patients treated with PTU, 7 patients treated with MMI, and all 14 patients. The horizontal axis lists the ICAM-1 concentrations in ng/ml. Values are means ±SE.

Serum levels of ICAM-1 were significantly higher in patients with psoriasis (515.21$\pm$51.26 ng/ml) than in normal control volunteers (366.78$\pm$20.71 ng/ml, P<0.04). ICAM-1 concentrations in serum did not fall significantly in the group as a whole after treatment with PTU or MMI (515.21$\pm$51.26 ng/ml baseline, versus 589.29$\pm$79.90 ng/ml post-treatment, P=ns). Separate pre- and post-treatment ICAM-1 concentrations in patients treated with either PTU or methimazole are shown in FIG. 15.

No significant difference was found between ICAM-1 concentrations between men and women in the control population. Serum ICAM-1 concentrations, either in the baseline state or after treatment with thioureylenes, did not correlate significantly with either the severity of the disease or the duration of the psoriasis.

Thus, as shown in example 11, PTU and MMI did not reduce the serum ICAM-1 concentrations in patients with psoriasis, indicating that the salutary effects of these thioureylenes on the clinical response of patients with psoriasis is exerted at a point distal to the early immune response that is characterized by enhanced ICAM-1 expression in the cellular components of the psoriatic lesions.

EXAMPLE 12

Evaluation of Side Effects of Thioureylene Therapy

Because of the known anti-thyroid effects of thioureylene therapy, patients were monitored for side effects. Serum TSH concentration was measured every 2 weeks during therapy, and a CBC was performed at the end of the study to monitor for cytopenia.

None of the patients experienced any significant side effects. Two patients became mildly hypothyroid (biochemical) while on the antithyroid thioureylenes between the sixth and eighth week of treatment. Neither of these two patients complained of symptoms suggestive of clinical hypothyroidism. Drug-induced cytopenia, which has been reported to occur in 1 in 500 to 1,000 patients on antithyroid thioureylenes, was not observed in any of the subjects.

Examples 3 and 4 demonstrate that PTU and MMI do not act to reduce the production of either IL2R or ICAM-1 in patients with psoriasis. However, I do not wish to exclude the use of those thioureylenes which do act to reduce either IL2R or ICAM-1 in the treatment of psoriasis or other auto-immune disorders.

THIABENDAZOLE THERAPY

Thiabendazole (2-(4-thiazolyl)-1-H-benzimidazole) is a broad spectrum anthelmintic, used in the treatment of pinworm, threadworm, whipworm, roundworm, and hookworm infections, as well as in cutaneous larva migrans. Because central nervous system and other side effects occur quite frequently, long term systemic administration of thiabendazole is not recommended.

Because of the success in the treatment of psoriasis using drugs of the thioureylene class, and because of the similarity in structure between thiabendazole and drugs of the thioureylene class, I believe that thiabendazole therapy is also effective in the treatment of psoriasis.

EXAMPLE 13

Effectiveness of Thiabendazole Therapy on Psoriasis 20 patients having stable plaque psoriasis are selected. These patients are free from other forms of topical therapy for psoriasis for at least two weeks, and free of systemic treatment for at least 4 weeks prior to the start of the study. The patients are randomly assigned to two groups. Patients in the first group receive thiabendazole (Merck, Sharp & Dohme, West Point, Pa.) administered topically, while those in the second group receive a placebo. The allocation is done in a double-blinded manner so that which patient receives thiabendazole and which receives placebo is not known until the end of the study.

At the start of the study, 5 mm punch biopsies are obtained from a representative area of the psoriatic plaque. The biopsies are used for a standard histological study (H & E stain). The clinical severity of the psoriasis is assessed using Psoriasis Area Severity Index (PASI) scores. The scoring is performed by 2 dermatologists and the mean of the 2 scores obtained is recorded.

Patients receive thiabendazole in topical form for 8 weeks. Skin biopsies are obtained at the end of 8 weeks of thiabendazole therapy for routine H & E examination. Follow-up clinical assessment (PASI scoring) is also done at the end of the 8 week treatment period.

A significant improvement in condition at the end of the treatment period is seen in those patients treated with thiabendazole. In this group, a decrease in the PASI score is seen, and patients report a decrease in the pain and itch of their plaques. A decrease in the thickness and scaling of the plaques should be seen as well. No significant change is seen in the PASI score in those patients receiving placebo, and no decrease in the pain, itch, thickness or scaling of the plaques reported.

TREATMENT OF AUTOIMMUNE DISEASES

Autoimmune disease is any of a group of disorders in which tissue injury is associated with humoral or cell-mediated responses to the body's own constituents. These disorders may be systemic, as in systemic lupus erythematosus, or organ specific, as in autoimmune thyroiditis.

Rheumatic disease, a type of autoimmune disease, is any of a variety of disorders characterized by inflammation, degeneration, or metabolic derangement of the connective tissue structures of the body, especially the joints and their related structures. The disease is attended by pain, stiffness, or limitation of motion in these parts.

Transplant rejection is an immune reaction seen in those patients receiving an organ or tissue graft from another individual. In hyperacute rejection, there is an immediate response against the graft because of the presence of preformed antibody, resulting in fibrin deposition, platelet aggregation, neutrophilic infiltration, and eventually, graft failure. In acute rejection, the response occurs after the sixth day and then proceeds rapidly. It is characterized by loss of function of the transplanted organ, and by pain and swelling. In chronic rejection, there is gradual progressive loss of function of the transplanted organ with less severe symptoms than in the acute form.

Because of the success in the treatment of psoriasis using drugs of the thioureylene class, and because of the immune system involvement in both psoriasis and autoimmune disease, I believe that thioureylene therapy is also effective in the treatment of autoimmune disease.

EXAMPLE 14

Effectiveness of Thioureylene Therapy on Rheumatoid Arthritis 10 patients diagnosed with rheumatoid arthritis are enrolled in the study. 100 mg propylthiouracil (Lederle Laboratories, Wayne N.J.) is administered every eight hours for the next eight weeks. Blood is removed every two weeks in order to monitor thyroid and bone marrow function.

Clinical evaluation is performed at the beginning and end of the study. Evaluation includes determining the presence of rheumatoid factor (RF) by latex agglutination in the sera of the patients enrolled in the study. Other diagnostic tests include sedimentation rate, x-rays, and examination of joint fluid.

A significant improvement in condition at the end of the treatment period is seen in the majority of the patients. A decrease in the RF titer should be seen, and patients should report a decrease in the pain and swelling of affected joints after 8 weeks of PTU therapy.

EXAMPLE 15

Effectiveness of Thioureylene Therapy on Systemic Lupus Erythematosus 10 patients diagnosed with systemic lupus erythematosus are enrolled in the study. 100 mg propylthiouracil (Lederle Laboratories, Wayne N.J.) is administered every eight hours for the next eight weeks. Blood is removed every two weeks in order to monitor thyroid and bone marrow function.

Clinical evaluation is performed at the beginning and end of the study. Evaluation includes identification of the presence of autoantibodies to nuclear antigens (ANA) through indirect immunofluorescence.

A significant improvement in condition at the end of the treatment period is seen in the majority of patients. A decrease in the ANA titer is seen, and patients should report a decrease in pain and inflammation after 8 weeks of PTU therapy.

EXAMPLE 16

Effectiveness of Thioureylene Therapy on Transplant Rejection 10 patients diagnosed with transplant rejection are enrolled in the study. 100 mg propylthiouracil (Lederle Laboratories, Wayne N.J.) is administered every eight hours for the next eight weeks. Blood is removed every two weeks in order to monitor thyroid and bone marrow function.

Clinical evaluation is performed at the beginning and end of the study. Evaluation includes identification of the presence of cytotoxic antibodies in the serum of the recipient which react with the lymphocytes of the donor.

A significant improvement in condition at the end of the treatment period is seen in the majority of patients. A decrease in the cytotoxic antibody titer is seen, and patients report a decrease in pain and inflammation after 8 weeks of PTU therapy.

While daily dosages of 300 mg propylthiouracil and 100 mg methimazole are used in the examples disclosed herein, these quantities should not be construed as limiting the scope of the invention. Administration of smaller or larger quantities can be required in order to observe a similar effect. Those of ordinary skill in the art will make adjustments to the quantity of drug delivered according to standard drug titration techniques. The determination of optimum dosage amounts and preparation of standard dose/response curves are well known exercises in the pharmaceutical arts.

Because of the immune modulatory effects of thioureylenes, bone marrow suppression and hypothyroidism may occur in some patients receiving thioureylene therapy. Therefore, bone marrow and thyroid functions should be monitored, and dosages adjusted accordingly, throughout thioureylene therapy. Methods used to monitor both bone marrow and thyroid function are well known to those skilled in the art.

Although certain examples have been used to illustrate and describe the present invention, it is intended that the scope of the invention not be limited to the specific examples set forth herein. Accordingly, the scope of the invention is intended to be defined only by the claims which follow.

I claim:

1. A method of treatment of psoriasis in a mammalian patient suffering from psoriasis, comprising the step of:
   administering to said patient an effective psoriasis-reducing amount of a thioureylene compound.

2. The method of claim 1, wherein the administering step comprises systemic administration.

3. The method of claim 1, wherein the administering step comprises topical administration to psoriasis-affected skin of said patient.

4. The method of claim 1, wherein said psoriasis is selected from the group consisting of p. annularis, p. arthropathica, p. buccalis, p. discoidea, p. figurata, flexural psoriasis, p. follicularis, guttate psoriasis, p. gyrata, inverse psoriasis, p. inveterata, p. linguae, p. ostracea, p. palmaris et plantaris, pustular psoriasis, p. rupioides, p. universalis, small plaque psoriasis, and large plaque psoriasis.

5. The method of claim 1, wherein said thioureylene compound is selected from the group consisting of propylthiouracil, methimazole, methylthiouracil and carbimazole.

6. The method of claim 2, wherein the administering step comprises administration of from 0.01 mg/kg to 100 mg/kg per day of said compound.

7. The method of claim 6, wherein said amount is from 0.1 mg/kg to 10 mg/kg.

* * * * *